(12) United States Patent
Utima et al.

(10) Patent No.: US 10,596,082 B2
(45) Date of Patent: Mar. 24, 2020

(54) ORAL CARE COMPOSITIONS AND METHODS OF USE

(71) Applicant: Colgate-Palmolive Company, New York, NY (US)

(72) Inventors: Enzo Utima, Sao Paulo (BR); Tatiana Cinquetti, Sao Paulo (BR); Fernanda Correa, Sao Paulo (BR); Paulo Focassio, Sao Paulo (BR); Debora Pedroso, Sao Paulo (BR)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 16/487,224

(22) PCT Filed: Feb. 21, 2018

(86) PCT No.: PCT/US2018/018896
§ 371 (c)(1),
(2) Date: Aug. 20, 2019

(87) PCT Pub. No.: WO2018/156545
PCT Pub. Date: Aug. 30, 2018

(65) Prior Publication Data
US 2020/0009030 A1    Jan. 9, 2020

Related U.S. Application Data

(60) Provisional application No. 62/461,577, filed on Feb. 21, 2017.

(51) Int. Cl.
*A61K 8/19* (2006.01)
*A61K 8/34* (2006.01)
*A61Q 11/00* (2006.01)
*A61K 8/365* (2006.01)

(52) U.S. Cl.
CPC .................. *A61K 8/19* (2013.01); *A61K 8/34* (2013.01); *A61K 8/345* (2013.01); *A61K 8/365* (2013.01); *A61Q 11/00* (2013.01)

(58) Field of Classification Search
None
See application file for complete search history.

(56) References Cited

U.S. PATENT DOCUMENTS

| 9,795,554 | B2 | 10/2017 | Nesta |
| 10,123,956 | B2 | 11/2018 | Kocinska et al. |
| 2013/0064779 | A1 | 3/2013 | Yamane |
| 2019/0046425 | A1 | 2/2019 | Kocinska et al. |

FOREIGN PATENT DOCUMENTS

| WO | 2011/152819 | 12/2011 |
| WO | 2014/088536 | 6/2014 |
| WO | 2015/172342 | 11/2015 |
| WO | 2016/105389 | 6/2016 |

OTHER PUBLICATIONS

International Search Report and Written Opinion of the International Searching Authority in International Application No. PCT/US2018/018896, dated May 17, 2018.

*Primary Examiner* — Nannette Holloman

(57) ABSTRACT

Disclosed herein are improved oral care formulations comprising precipitated calcium carbonate (PCC) and preservative combinations selected from the group consisting of i) phenethyl alcohol and caprylyl glycol, and ii) benzyl alcohol and caprylyl glycol. Methods of making and using the compositions are also provided.

14 Claims, No Drawings

ORAL CARE COMPOSITIONS AND METHODS OF USE

FIELD

This invention relates to improved oral care formulations comprising precipitated calcium carbonate (PCC) and preservatives selected from the group consisting of i) phenethyl alcohol and caprylyl glycol, and ii) benzyl alcohol and caprylyl glycol as well as to methods of using and of making these compositions.

BACKGROUND

Precipitated calcium carbonate (PCC) is manufactured on a commercial scale for use in a variety of industrial, cosmetic and pharmaceutical products. Slurries of precipitated calcium carbonate, such as used in oral care compositions, are susceptible to microorganism contamination. To reduce the amount of viable microorganisms, a preservative, such as aldehyde, can be added to the slurry. For example, U.S. Patent Application Publication No. 2009/0088483 discloses combinations of a dialdehyde (such as glutaraldehyde) and a formaldehyde-releasing agent, such as (ethylenedioxy) dimethanol. Unfortunately, these preservatives have their limitations. Glutaraldehyde, for example, is unstable at alkaline pH, and is therefore ineffective as a long-term preservative for this kind of material. Furthermore, some bacterial strains metabolize formaldehyde (see, for example, Di Maiuta et al. (2009) International Biodeterioration & Biodegradation 63:769-777), permitting bacterial growth even in a treated PCC slurry.

Thus, there is a need for improved preservation ingredients for use in precipitated calcium carbonate containing compositions.

SUMMARY OF THE INVENTION

It has been surprisingly found that the inclusion of certain ingredient components within precipitated calcium carbonate containing oral care compositions may minimize microbial growth within the oral care composition. Minimization of microbial growth from an oral care product, such as a dentifrice formulation, may be useful for use in prolonging the shelf-life and ensuring the quality of oral care compositions.

In one embodiment, the invention is an oral care composition comprising precipitated calcium carbonate (PCC) and a combination of preservatives selected from the group consisting of i) phenethyl alcohol and caprylyl glycol, and ii) benzyl alcohol and caprylyl glycol. In certain embodiments, the oral care composition is a dentifrice.

In certain embodiments, the PCC in the oral care composition is present in an amount of 30-45% by weight of the composition. In further embodiments, PCC in the oral care composition is present in an amount of 30-45% by weight of the composition and phenethyl alcohol is present in an amount of 0.1 to 1.0% by weight of the composition. In further embodiments, PCC in the oral care composition is present in an amount of 30-45% by weight of the composition, phenethyl alcohol is present in an amount of 0.1 to 1.0% by weight of the composition and caprylyl glycol is present in an amount of 0.1 to 1.0% by weight of the composition. In yet further embodiments, phenethyl alcohol is present in an amount of 0.2 to 0.3% by weight of the composition and caprylyl glycol is present in an amount of 0.13 to 0.2% by weight of the composition.

In certain embodiments, PCC in the oral care composition is present in an amount of 30-45% by weight of the composition and benzyl alcohol is present in an amount of 0.1 to 1.0% by weight of the composition. In further embodiments, PCC in the oral care composition is present in an amount of 30-45% by weight of the composition, benzyl alcohol is present in an amount of 0.1 to 1.0% by weight of the composition and caprylyl glycol is present in an amount of 0.1 to 1.0% by weight of the composition. In further embodiments, benzyl alcohol is present in an amount of 0.2 to 0.3% by weight of the composition and caprylyl glycol is present in an amount of 0.13 to 0.2% by weight of the composition.

In certain embodiments, the oral care composition of any of the preceding embodiments further comprises a humectant present in an amount of 10.0 to 30.0% by weight of the composition. In certain embodiments, the oral care composition of any of the preceding embodiments further comprises a surfactant present in an amount of 1.0 to 6.0% by weight of the composition. In certain embodiments, the oral care composition of any of the preceding embodiments further comprises a flavor present in an amount of 0.5 to 2.0% by weight of the composition.

In certain embodiments, the invention is a method to improve oral health comprising applying an effective amount of the oral care composition of any of the preceding embodiments set forth to the oral cavity of a subject in need thereof. In certain embodiments improving oral health may be selected from one or more of the following: a) reduce or inhibit formation of dental caries; b) reduce, repair or inhibit early enamel lesions; c) reduce or inhibit demineralization and promote remineralization of the teeth; d) reduce hypersensitivity of the teeth; e) reduce or inhibit gingivitis; f) promote healing of sores or cuts in the mouth; g) reduce levels of acid producing bacteria; h) to increase relative levels of arginolytic bacteria; i) inhibit microbial biofilm formation in the oral cavity; j) raise and/or maintain plaque pH at levels of at least pH 5.5 following sugar challenge; k) reduce plaque accumulation; l) treat, relieve or reduce dry mouth, m) whiten teeth; n) enhance systemic health, including cardiovascular health; o) reduce erosion of the teeth; p) immunize the teeth against cariogenic bacteria and their effects; q) clean the teeth and oral cavity; r) reduce inflammation; and s) increase anti-oxidant levels.

In certain embodiments, the invention is a composition obtained or obtainable by combining the ingredients as set forth in any of the preceding compositions and methods.

DETAILED DESCRIPTION

The following description of embodiment(s) of the invention is merely exemplary in nature and is in no way intended to limit the invention, its application, or uses.

All references cited herein are hereby incorporated by reference in their entireties. In the event of a conflict in a definition in the present disclosure and that of a cited reference, the present disclosure controls.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used throughout, ranges are used as shorthand for describing each and every value that is within the range. Any value within the range can be selected as the terminus of the range.

Unless stated otherwise, all percentages of composition components given in this specification are by weight based on a total composition or formulation weight of 100%. The term "wt %" is an abbreviation for weight percent. For example, "molecule A 40 wt %" is meant to exemplify a molecule A having 40% weight of a total composition or formulation of 100%. Further, molecule A 40 wt % will constitute 40 g of molecule A in a 100 g total composition of formulation.

As used herein, the term "oral composition" means the total composition that is delivered to the oral surfaces. The composition is further defined as a product which, during the normal course of usage, is not for the purposes of systemic administration of particular therapeutic agents, intentionally swallowed but is rather retained in the oral cavity for a time sufficient to contact substantially all of the dental surfaces and/or oral tissues for the purposes of oral activity. Examples of such compositions include, but are not limited to, a dentifrice, a mouthwash or a mouth rinse, a topical oral gel, a denture cleanser, dental strips, beads, varnish, toothpowder and the like.

As used herein, the term "dentifrice" means paste, powder, gel, or liquid formulations unless otherwise specified. In certain embodiments, the dentifrice is toothpaste. The dentifrice composition can be in any desired form such, as deep striped, surface striped, multi-layered, having the gel surrounding the paste, or any combination thereof. Alternatively, the oral composition may be dual phase dispensed from a separated compartment dispenser.

In preferred embodiments of this invention, the oral composition is a dentifrice. Such dentifrices may include toothpowder, a dental tablet, toothpaste (dental cream), or gel, or any other known form known to one of skill in the art.

The term "effective amount" as used herein means that the amount of the composition of the present invention is of sufficient quantity to achieve the intended purpose, such as, for example, to induce or cause teeth whitening in the subject.

The compositions and formulations as provided herein are described and claimed with reference to their ingredients, as is usual in the art. As would be evident to one skilled in the art, the ingredients may in some instances react with one another, so that the true composition of the final formulation may not correspond exactly to the ingredients listed. Thus, it should be understood that the invention extends to the product of the combination of the listed ingredients.

The oral care compositions of the present invention utilize precipitated calcium carbonate as an abrasive. The precipitated calcium carbonate particles are present in an amount of from 30 to 45 wt % based on the weight of the composition, further optionally from 35 to 40 wt % based on the weight of the composition. In certain embodiments, the calcium carbonate particles are present in an amount of from 40 to 45 wt % based on the weight of the composition. In further embodiments, the calcium carbonate particles are present in an amount of about 42 wt % based on the weight of the composition.

It has been surprisingly discovered that a low concentration of certain ingredient combinations, e.g., benzyl alcohol and caprylyl glycol, each at 0.1 to 1.0 wt % in one embodiment, more preferably benzyl alcohol at 0.2 to 0.3 wt % and caprylyl glycol at 0.13 to 0.2 wt % in another embodiment; phenethyl alcohol and caprylyl glycol, each at 0.1 to 1.0 wt % in one embodiment, more preferably, phenethyl alcohol at 0.2 to 0.3 wt % and caprylyl glycol at 0.13 to 0.2 wt % in another embodiment, can reduce microbial contamination in oral care compositions containing precipitated calcium carbonate.

In one embodiment, the invention provides an oral care composition comprising PCC and a combination of preservatives selected from the group of i) phenethyl alcohol and caprylyl glycol, and ii) benzyl alcohol and caprylyl glycol; and optionally an orally acceptable carrier. In certain embodiments, the combination of preservatives is phenethyl alcohol and caprylyl glycol. In certain embodiments, the combination of preservatives is benzyl alcohol and caprylyl glycol. In certain embodiments, the oral care composition further comprises one or more ingredient categories selected from humectants, surfactants and flavors.

The present invention provides compositions comprising an orally acceptable carrier. As used herein, an "orally acceptable carrier" refers to a material or combination of materials that are safe for use in the compositions of the present invention, commensurate with a reasonable benefit/risk ratio. Preferably, the carrier does not substantially reduce the efficacy of the ingredients within the oral care composition, such as a peroxide complex or whitening agent. Selection of specific carrier components is dependent on the desired product form, including dentifrices, rinses, gels, and paints. In various embodiments, the carrier is operable to sufficiently adhere the peroxide complex against surfaces within the oral cavity to which the composition is administered, without concomitant use of a dental tray, mouthpiece, tape, or similar appliance. In various embodiments, the carrier is operable for use with a tape, tray, mouthpiece or similar appliance.

Materials among those that are useful in carriers include adhesion agents, viscosity modifiers, diluents, surfactants, foam modulators, peroxide activators, peroxide stability agents, abrasives, pH modifying agents, humectants, mouth feel agents, sweeteners, flavorants, colorants, and combinations thereof. It is understood that while general attributes of each of the above categories of materials may differ, there may be some common attributes and any given material may serve multiple purposes within two or more of such categories of materials. Preferably, such carrier materials are selected for compatibility with the peroxide complex and with other ingredients of the composition.

In various preferred embodiments, the orally acceptable carrier may comprise polymers and/or copolymers of polyethylene glycol, of ethylene oxide propylene oxide, and of silicone. If such copolymers/polymers are used, they may be selected from the commercially available materials PLURAFLO® L4370 and PLURAFLO® L1220 (available from BASF, Wyandotte, Mich., United States of America). In one embodiment such polymer and/or copolymer is an ethylene oxide, propylene oxide block co-polymer of formula (ethylene oxide)x-(propylene oxide)y wherein x is an integer of 80-150, e.g. 100-130, e.g. about 118, and y is an integer 30-80, e.g. about 60-70, e.g. about 66, having an average molecular weight of greater than 5000, e.g., 8000-13000 Da, e.g. about 9800. Block copolymers of ethylene oxide/propylene oxide are useful, but higher molecular weight, e.g., >5000 Da are preferred, e.g. including PLURACARE® L1220 (available from BASE, Wyandotte, Mich., United States of America). Low or medium molecular weight polyethylene glycol, e.g., PEG 400, PEG 600, PEG 800, PEG 1000 and mixtures thereof are also useful. It is preferred that the carrier(s) provide a dentifrice with a viscosity of about 10,000 CPS to about 700,000 CPS, preferably about 30,000 CPS to about 300,000 CPS.

The toothpaste compositions may further comprise, in addition to the precipitated calcium carbonate particles, one or more further abrasive particulates. Any abrasive particulates may be used and may be selected from sodium bicarbonate, calcium phosphate (e.g., dicalcium phosphate dihydrate), calcium pyrophosphate calcium sulfate, silica, iron oxide, aluminium oxide, perlite, plastic particles, e.g., polyethylene, and combinations thereof. Any type of silica may be used, such as hydrated silica, precipitated silica or silica gel. Optionally, the oral care composition further comprises, as a thickener and also as an abrasive, silica particles in an amount of from 1 to 3 wt % based on the weight of the composition.

Certain abrasives may be used which portray dual functionality. In one embodiment, the toothpaste composition comprises silica that has a particle size and an amount and distribution in the toothpaste composition so that the silica has a dual function, and functions not only as a dentin tubule-occluding particulate but also as an abrasive particulate. Such a dual function particulate may be provided by a commercially available silica such as INEOS AC43 (Ineos Silicas, Warrington, United Kingdom). In an embodiment, such silica has a median particle size less than 8 µm, for example from 3 µm to 5 µm.

The compositions of the present invention may further comprise an abrasive useful for example as a polishing agent. Any orally acceptable abrasive can be used, but type, fineness, (particle size) and amount of abrasive should be selected so that tooth enamel is not excessively abraded in normal use of the composition. Suitable abrasives include silica, for example in the form of precipitated silica or as admixed with alumina, insoluble phosphates, and mixtures thereof. Among insoluble phosphates useful as abrasives are orthophosphates, polymetaphosphates and pyrophosphates. Illustrative examples are dicalcium orthophosphate dihydrate, calcium pyrophosphate, calcium pyrophosphate, tricalcium phosphate, calcium polymetaphosphate and insoluble sodium polymetaphosphate.

In an embodiment, the abrasive particles may be initially present in the oral care composition, for example, a toothpaste, having the desired particle size, or may be initially present in the composition at a larger size, so long as the structure of the particles is such that it fractures or breaks into the desired particle size upon application of mechanical force by, e.g., a toothbrush, when brushing. In some embodiments, the dentifrice contains one or more humectants.

In some embodiments, the present invention further provides oral care compositions comprising: a cross-linked polyvinylpyrrolidone complexed with hydrogen peroxide, a stabilizing amount of an additional linear and/or cross-linked polyvinylpyrrolidone, precipitated calcium carbonate (PCC) and preservatives selected from the group consisting of i) phenethyl alcohol and caprylyl glycol, and ii) benzyl alcohol and caprylyl glycol.

The invention may contain whitening agents. Some embodiments provide non-aqueous dentifrice compositions comprising from 5 to 20 wt % cross-linked polyvinylpyrrolidone complexed with hydrogen peroxide (PVP—$H_2O_2$). Other embodiments provide oral care compositions comprising from 5 to 12 wt % cross-linked polyvinylpyrrolidone complexed with hydrogen peroxide. Still other embodiments provide oral care compositions comprising from 9 to 12 wt % cross-linked polyvinylpyrrolidone complexed with hydrogen peroxide. Yet other embodiments provide non-aqueous dentifrice compositions comprising 11 wt % cross-linked polyvinylpyrrolidone complexed with hydrogen peroxide.

In some embodiments, the present invention provides non-aqueous dentifrice compositions comprising from 0.03 to about 3 wt % of an additional linear and/or crosslinked polyvinylpyrrolidone. Some embodiments provide compositions comprising 1.75 wt %, by weight, of an additional linear and/or cross-linked polyvinylpyrrolidone.

The invention may contain additional whitening agents in addition to PVP—$H_2O_2$. Any whitening agent known or developed in the art may be used. Preferably, the whitening agent includes solid whitening agents and bound whitening agents which are substantially anhydrous oxygen generating compounds. Solid whitening agents useful herein include peroxides, metal chlorites, persulfate. Exemplary peroxide phases include hydroperoxides, hydrogen peroxide, peroxides of alkali and alkaline earth metals, organic peroxy compounds, peroxy acids, pharmaceutically-acceptable salts thereof, and mixtures thereof. Peroxides of alkali and alkaline earth metals include lithium peroxide, potassium peroxide, sodium peroxide, magnesium peroxide, calcium peroxide, barium peroxide, and mixtures thereof. Organic peroxy compounds include urea peroxide, glyceryl hydrogen peroxide, alkyl hydrogen peroxides, dialkyl peroxides, alkyl peroxy acids, peroxy esters, diacyl peroxides, benzoyl peroxide, and monoperoxyphthalate, and mixtures thereof. Peroxy acids and their salts include organic peroxy acids such as alkyl peroxy acids, and monoperoxyphthalate and mixtures thereof, as well as inorganic peroxy acid salts such as and perborate salts of alkali and alkaline earth metals such as lithium, potassium, sodium, magnesium, calcium and barium, and mixtures thereof. Preferred solid peroxides are sodium perborate, urea peroxide, and mixtures thereof. Suitable metal chlorites include calcium chlorite, barium chlorite, magnesium chlorite, lithium chlorite, sodium chlorite, and potassium chlorite. The whitening agent may be preferably bound. For example, peroxide may be bound to a polymer such as PVP (poly(N-vinylpyrrolidone)). Suitable PVP complexes are disclosed, for example, in U.S. Pat. No. 5,122,370, the contents of which are incorporated herein by reference. In some embodiments, it may be desirable to use any known whitening agent except sodium percarbonate and/or any of the percarbonate salts.

In various preferred embodiments, the non-aqueous dentifrice comprises a substantially anhydrous orally acceptable carrier and various dentifrice ingredients to adjust the rheology and feel of the composition such as humectants, surface active agents, thickening or gelling agents, etc.

Flavorants, sweeteners, colorants, foam modulators, mouth-feel agents and others additively may be included if desired, in the composition.

The oral care composition can optionally include at least one orally acceptable source of fluoride ions. Any known or to be developed in the art may be used. Suitable sources of fluoride ions include fluoride, monofluorophosphate and fluorosilicate salts. One or more fluoride ion-releasing compound is optionally present in an amount providing a total of about 100 to about 20,000 ppm, about 200 to about 5,000 ppm, or about 500 to about 2,500 ppm, fluoride ions.

The compositions of the present invention optionally comprise an antimicrobial (e.g., antibacterial) agent. A further illustrative list of useful antibacterial agents is provided in such as those listed in U.S. Pat. No. 5,776,435 to Gaffar et al., the contents of which are incorporated herein by reference. One or more antimicrobial agents are optionally present in an antimicrobial effective total amount, typically about 0.05% to about 10%, for example about 0.10% to about 3%.

The compositions of the present invention optionally comprise an antioxidant. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

The compositions of the present invention optionally comprise a sialagogue or saliva-stimulating agent, an anti-plaque agent, an anti-inflammatory agent, a desensitizing.

In various embodiments of the present invention, the oral composition comprises an anticalculus (tartar control) agent. Generally, tartar control agents are categorized as being incompatible with some whitening agents, but embodiments of the present invention incorporate tartar control agents and whitening agents in a single phase whitening composition. Suitable anticalculus agents include without limitation phosphates and polyphosphates (for example pyrophosphates), polyaminopropanesulfonic acid (AMPS), hexametaphosphate salts, zinc citrate trihydrate, polypeptides, polyolefin sulfonates, polyolefin phosphates, diphosphonates. In some embodiments the anticalculus agent is present at about 0.1% to about 30%. The oral composition may include a mixture of different anticalculus agents. In one preferred embodiment, tetrasodium pyrophosphate (TSPP) and/or sodium acid pyrophosphate (SAPP) are used. In the one embodiment, the anticalculus agent comprises TSPP at about 1-2% and SAPP at about 0.5 to 5%. In a second preferred embodiment, tetrasodium pyrophosphate (TSPP) and/or sodium tripolyphosphate (STPP) are used. In the second preferred embodiment, the anticalculus agent comprises TSPP at about 1-2% and STPP at about 7% to 10%.

The compositions of the present invention optionally comprise a thickener. Any orally acceptable thickening agent can be used, including without limitation carbomers, also known as carboxyvinyl polymers, carrageenans, also known as Irish moss and more particularly-carrageenan (iota-carrageenan), high molecular weight polyethylene glycols (such as CARBOWAX®, available from The Dow Chemical Company), cellulosic polymers such as hydroxyethylcellulose, carboxymethylcellulose (CMC) and salts thereof, e.g., CMC sodium, natural gums such as karaya, xanthan, gum arabic and tragacanth, colloidal magnesium aluminum silicate, and colloidal and/or fumed silica and mixtures of the same. One or more thickening agents are optionally present in a total amount of about 0.1% to about 90%, for example about 1% to about 50% or about 5% to about 35%.

Thickening agents suitable for use in the compositions of the present invention include natural and synthetic gums and colloids. Suitable thickening agents include naturally occurring polymers such as carrageenan, xanthan gum, polyglycols of varying molecular weights sold under the tradename Polyox, and polyvinylpyrrolidone. Compatible inorganic thickening agents include amorphous silica compounds which function as thickening agents and include colloidal silicas compounds available under the trade designation Cab-o-sil (Cabot Corporation and distributed by Lenape Chemical, Bound Brook, N.J.), Zeodent 165 (J. M. Huber Chemicals Division, Havre de Grace, Md.); and Sylodent 15 (Davison Chemical Division of W. R. Grace Corporation, Baltimore, Md.). Other inorganic thickening agents include natural and synthetic clays such as hectorite clays, lithium magnesium silicate (laponite) and magnesium aluminum silicate (Veegum). In certain embodiments, the thickening agent may be selected from carrageenan (Iris moss), xanthan gum, starch, polyvinyl pyrrolidone and amorphous silicas, or any combination thereof.

While ingredients are sometimes identified herein by category, e.g., humectant, antioxidant, thickener, etc., this identification is for convenience and clarity, but is not intended to be limiting. All of the ingredients in the compositions may have functions in addition to their primary function, and may contribute to the overall properties of the composition, including its stability, efficacy, consistency, mouth feel, taste, odor and so forth.

In some embodiments, the sweetener may be sodium saccharin.

In certain embodiments, the buffering agents may be a sodium phosphate buffer (e.g., sodium phosphate monobasic and disodium phosphate).

Surfactants may be included, if desired. Examples of suitable surfactants include water-soluble salts of higher fatty acid monoglyceride monosulfates, such as the sodium salt of monosulfated monoglyceride of hydrogenated coconut oil fatty acids; higher alkyl sulfates such as sodium lauryl sulfate; alkyl aryl sulfonates such as sodium dodecyl benzene sulfonate; higher alkyl sulfoacetates, such as sodium lauryl sulfoacetate; higher fatty acid esters of 1,2-dihydroxypropane sulfonate; and the substantially saturated higher aliphatic acyl amides of lower aliphatic amino carboxylic compounds, such as those having 12-16 carbons in the fatty acid, alkyl or acyl radicals; and the like. Examples of the last mentioned amides include N-lauryl sarcosine, and the sodium, potassium and ethanolamine salts of N-lauryl, N-myristoyl, or N-palmitoyl sarcosine. Others include, for example, nonanionic polyoxyethylene surfactants, such as Polyoxamer 407, Steareth 30, Polysorbate 20, and castor oil; and amphoteric surfactants, such as cocamidopropyl betaine (tegobaine), and cocamidopropyl betaine lauryl glucoside; condensation products of ethylene oxide with various hydrogen containing compounds that are reactive therewith and have long hydrocarbon chains (e.g., aliphatic chains of from 12 to 20 carbon atoms), which condensation products (ethoxamers) contain hydrophilic polyoxyethylene moieties, such as condensation products of poly (ethylene oxide) with fatty acids, fatty, alcohols, fatty amides and other fatty moieties, and with propylene oxide and polypropylene oxides. In some embodiments, the surfactant may be sodium lauryl sulfate (SLS). In further embodiments, suitable surfactants include, without limitation, water-soluble salts of ethylene-20 alkyl sulfates, sulfonated monoglycerides of C8-20 fatty acids, sarcosinates, taurates, sodium lauryl sulfate, sodium coroyl monoglyceride sulfonate, sodium lauryl sarcosinate, sodium lauryl isoethionate, sodium laureth carboxylate and sodium dodecyl benzenesulfonate, and cocoamidopropyl betaine.

The oral care compositions of the invention may also include a flavoring agent. Flavoring agents which are used in the practice of the present invention include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint. The flavoring agent is incorporated in the oral composition at a concentration of 0.1 to about 5% by weight. In certain embodiments, the flavoring agent is incorporated at 0.5 to 2.0% by weight.

pH modifying agents among those useful herein include acidifying agents to lower pH, basifying agents to raise pH, and buffering agents to control pH within a desired range. For example, one or more compounds selected from acidifying, basifying and buffering agents can be included to provide a pH of 2 to 10, or in various embodiments from 2 to 8, from 3 to 9, from 4 to 8, from 5 to 7, from 6 to 10, and from 7 to 9. Any orally acceptable pH modifying agent can be used, including without limitation carboxylic, phosphoric and sulfonic acids, acid salts (e.g., monosodium citrate, disodium citrate, monosodium malate, etc.), alkali metal hydroxides such as sodium hydroxide, carbonates such as sodium carbonate, bicarbonates, sesquicarbonates, borates, silicates, phosphates (e.g., monosodium phosphate, trisodium phosphate, pyrophosphate salts, etc.), imidazole and mixtures thereof. One or more pH modifying agents are optionally present in a total amount effective to maintain the composition in an orally acceptable pH range.

In certain aspects, methods are provided to improve oral health by applying an effective amount of any of the oral care composition described herein to the oral cavity of a subject in need thereof. In certain embodiments, the methods utilize an oral care composition comprising precipitated calcium carbonate (PCC), phenethyl alcohol and caprylyl glycol. In further embodiments, the PCC in the oral care composition is present in an amount of 30-45% by weight of the composition. In further embodiments, PCC in the oral care composition is present in an amount of 30-45% by weight of the composition and phenethyl alcohol is present in an amount of 0.1 to 1.0% by weight of the composition. In further embodiments, PCC in the oral care composition is present in an amount of 30-45% by weight of the composition, phenethyl alcohol is present in an amount of 0.1 to 1.0% by weight of the composition and caprylyl glycol is present in an amount of 0.1 to 1.0% by weight of the composition. In yet further embodiments, phenethyl alcohol is present in an amount of 0.2 to 0.3% by weight of the composition and caprylyl glycol is present in an amount of 0.13 to 0.2% by weight of the composition.

In certain embodiments, the methods utilize an oral care composition comprising PCC, benzyl alcohol and caprylyl glycol. In further embodiments, the PCC is present in an amount of 30-45% by weight of the composition. In further embodiments, PCC in the oral care composition is present in an amount of 30-45% by weight of the composition and benzyl alcohol is present in an amount of 0.1 to 1.0% by weight of the composition. In further embodiments, PCC in the oral care composition is present in an amount of 30-45% by weight of the composition, benzyl alcohol is present in an amount of 0.1 to 1.0% by weight of the composition and caprylyl glycol is present in an amount of 0.1 to 1.0% by weight of the composition. In further embodiments, benzyl alcohol is present in an amount of 0.2 to 0.3% by weight of the composition and caprylyl glycol is present in an amount of 0.13 to 0.2% by weight of the composition.

In certain embodiments, the improvement in oral health may be selected from one or more of the following: a. reduce or inhibit formation of dental caries; b. reduce, repair or inhibit early enamel lesions; c. reduce or inhibit demineralization and promote remineralization of the teeth; d. reduce hypersensitivity of the teeth; e. reduce or inhibit gingivitis; f. promote healing of sores or cuts in the mouth; g. reduce levels of acid producing bacteria; h. to increase relative levels of arginolytic bacteria; i. inhibit microbial biofilm formation in the oral cavity; j. raise and/or maintain plaque pH at levels of at least pH 5.5 following sugar challenge; k. reduce plaque accumulation; l. treat, relieve or reduce dry mouth; m. whiten teeth; n. enhance systemic health, including cardiovascular health; o. reduce erosion of the teeth; p. immunize the teeth against cariogenic bacteria and their effects; q. clean the teeth and oral cavity; r. reduce inflammation; and s. increase anti-oxidant levels.

In one embodiment, the composition remains stable when stored for at least 1 week, at least 2 weeks, at least 1 month, at least 3 months, at least 6 months, or at least 1 year. In one embodiment, the composition is stored at room temperature.

In further embodiments, methods are provided to improve oral health of a human or animal subject comprising contacting any composition described herein with the oral surface of the human or animal subject. As used herein "animal subject" includes higher order non-human mammals such as canines, felines, and horses. The oral care composition is contacted with an oral surface of the mammalian subject to thereby improve oral health in a highly efficacious manner.

In various embodiments, it is preferred that the oral care composition is applied and contacted with the oral surface. The dentifrice, prepared in accordance with the present invention is preferably applied regularly to an oral surface, preferably on a daily basis, at least one time daily for multiple days, but alternately every second or third day. Preferably the oral composition is applied to the oral surfaces from 1 to 3 times daily, for at least 2 weeks up to 8 weeks, from four months to three years, or more up to lifetime.

The compositions of the invention can be packaged into containers or dispensers known in the art, via means conventional in the art. In some embodiments the compositions are packaged into tubes, metal, plastic or laminated, with either screw top or flip top caps.

EXAMPLES

Example 1—Preparation of Toothpaste

In a stainless steel bucket, water and humectant was first added and stirred using an overhead stirrer (EUROSTAR 200, IKA, North Carolina, USA) equipped with a cowles disperser. Mixing was started at 500 rpm for 1 minute. Gum and salts (buffering agents, sweetener, fluoride) were added next and the resulting solution was mixed at 1,000 rpm for 20 minutes to obtain a gel phase.

A fraction of the gel phase sample was transferred to a new stainless steel bucket. Using an overhead stirrer (EUROSTAR 200, IKA) equipped with a 4-bladed propeller stirrer, mixing was performed at 750 rpm for 1 minute. Next, to the mixture was added water, PCC slurry (previously contaminated for the study purpose), surfactant, and other ingredients (benzyl alcohol/caprylyl glycol or phenethyl alcohol/caprylyl glycol) and mixed for 15 minutes to obtain the final base.

TABLE 1

| | Formulations | |
|---|---|---|
| | Solution | |
| Ingredient | A<br>% by weight | B<br>% by weight |
| Water | 20.0 to 40.0 | 20.0 to 40.0 |
| Humectant | 10.0 to 30.0 | 10.0 to 30.0 |
| Sweetener | 0.10 to 0.50 | 0.10 to 0.50 |
| Thickeners (gums) | 0.50 to 2.00 | 0.50 to 2.00 |

TABLE 1-continued

Formulations

| Ingredient | Solution A % by weight | Solution B % by weight |
|---|---|---|
| Sodium Monofluorphoshate (MFP) | 1.10 | 1.10 |
| Additives (buffering agents, salts) | 0.50 to 2.00 | 0.50 to 2.00 |
| PCC (Precipitated Calcium Carbonate) | 30.0 to 45.0 | 30.0 to 45.0 |
| Surfactant | 1.00 to 6.00 | 1.00 to 6.00 |
| Benzyl alcohol | 0.10 to 1.00 | |
| Caprylyl Glycol | 0.10 to 1.00 | 0.10 to 1.00 |
| Phenethyl alcohol | | 0.10 to 1.00 |
| Flavor | 0.50 to 2.00 | 0.50 to 2.00 |

Example 2—Bactericidal Testing

Sample preparation was made by mixing 10 grams of the final base (see Example 1) with 90 mL of diluent (TAT broth (catalog #298410, BD) supplemented with 0.3% NaCl and 4% Tween) to achieve a 1:10 dilution. Serial dilutions of $10^{-1}$ to $10^{-6}$ were made in neutralizing broth (TAT supplemented with 0.3% NaCl), allowed to incubate for 0, 2, 4, 6, 24 and 48 hours, and plated in 15-20 mL of melted Modified Letheen Agar (MLA). Plates were swirled to allow complete dispersion and allowed to solidify. Solidified plates were then inverted and incubated at 30° C. for at least 48 hours. Colonies were counted using a Quebec colony counter (Phoenix Luferco, Brazil). Table 2 presents the study results, showing numbers of microorganisms per gram of product (CFU/) at different time points. Unexpectedly, the preservative effects of benzyl alcohol and caprylyl glycol are more than cumulative when compared to the preservative effect profile when each component is used individually. Further, use of phenethyl alcohol and caprylyl glycol in combination shows a similar unexpected enhancement in the preservative effect profile.

TABLE 2

Results of Bactericidal Analysis

| | 0 hr | 2 hr | 4 hr | 6 hr | 24 hr | 48 hr |
|---|---|---|---|---|---|---|
| Control | 13,300 | 13,300 | 14,600 | 21,500 | 15,600 | 8,400 |
| Benzyl alcohol (0.30%) | 13,300 | 18,250 | 13,000 | 8,000 | 3,650 | 125 |
| Caprylyl glycol (0.20%) | 13,300 | 14,000 | 1,200 | 2,100 | 435 | 80 |
| Phenethyl alcohol (0.30%) + Caprylyl glycol (0.20%) | 13,300 | 210 | 85 | 235 | 195 | 75 |
| Benzyl alcohol (0.30%) + Caprylyl glycol (0.20%) | 13,300 | 260 | 180 | 185 | 135 | 95 |
| Phenethyl alcohol (0.20%) + Caprylyl glycol (0.13%) | 13,300 | 380 | 90 | 230 | 255 | 105 |
| Benzyl alcohol (0.20%) + Caprylyl glycol (0.13%) | 13,300 | 960 | 610 | 680 | 415 | 175 |

While the present invention has been described with reference to embodiments, it will be understood by those skilled in the art that various modifications and variations may be made therein without departing from the scope of the present invention.

The invention claimed is:

1. An oral care composition comprising precipitated calcium carbonate (PCC) and a combination of preservatives, selected from the group consisting of;
   a) phenethyl alcohol and caprylyl glycol, and
   b) benzyl alcohol and caprylyl glycol.

2. The oral care composition of claim 1, wherein the composition is a dentifrice.

3. The oral care composition of claim 2, wherein said PCC is present in an amount of 30-45% by weight of the composition.

4. The oral care composition of claim 3, wherein said phenethyl alcohol is present in an amount of 0.1 to 1.0% by weight of the composition.

5. The oral care composition of claim 4, wherein said caprylyl glycol is present in an amount of 0.1 to 1.0% by weight of the composition.

6. The oral care composition of claim 5, wherein said phenethyl alcohol is present in an amount of 0.2 to 0.3% by weight of the composition and said caprylyl glycol is present in an amount of 0.13 to 0.2% by weight of the composition.

7. The oral care composition of claim 3, wherein said benzyl alcohol is present in an amount of 0.1 to 1.0% by weight of the composition.

8. The oral care composition of claim 7, wherein said caprylyl glycol is present in an amount of 0.1 to 1.0% by weight of the composition.

9. The oral care composition of claim 8, wherein said benzyl alcohol is present in an amount of 0.2 to 0.3% by weight of the composition and said caprylyl glycol is present in an amount of 0.13 to 0.2% by weight of the composition.

10. The oral care composition of claim 1, further comprising a humectant present in an amount of 10.0 to 30.0% by weight of the composition.

11. The oral care composition of claim 1, further comprising a surfactant present in an amount of 1.0 to 6.0% by weight of the composition.

12. The oral care composition of claim 1, further comprising a flavor present in an amount of 0.5 to 2.0% by weight of the composition.

13. A method to improve oral health comprising applying an effective amount of the oral care composition of claim 1 to the oral cavity of a subject in need thereof.

14. The method of claim 13, wherein improving oral health may be selected from one or more of the following;
   a. reduce or inhibit formation of dental caries;
   b. reduce, repair or inhibit early enamel lesions;
   c. reduce or inhibit demineralization and promote remineralization of the teeth;
   d. reduce hypersensitivity of the teeth;
   e. reduce or inhibit gingivitis;
   f. promote healing of sores or cuts in the mouth;
   g. reduce levels of acid producing bacteria;
   h. to increase relative levels of arginolytic bacteria;
   i. inhibit microbial biofilm formation in the oral cavity;
   j. raise and/or maintain plaque pH at levels of at least pH 5.5 following sugar challenge;
   k. reduce plaque accumulation;
   l. treat, relieve or reduce dry mouth;
   m. whiten teeth;
   n. enhance systemic health, including cardiovascular health;
   o. reduce erosion of the teeth;

p. immunize the teeth against cariogenic bacteria and their effects;
q. clean the teeth and oral cavity;
r. reduce inflammation; and
s. increase anti-oxidant levels.

\* \* \* \* \*